US00PP15256P2

(12) United States Plant Patent
Carruth

(10) Patent No.: US PP15,256 P2
(45) Date of Patent: Oct. 19, 2004

(54) MINIATURE ROSE PLANT NAMED 'WEKEMILCHO'

(50) Latin Name: *Rosa hybrida*
Varietal Denomination: WEKemilcho

(75) Inventor: Thomas F. Carruth, Altadena, CA (US)

(73) Assignee: Weeks Wholesale Rose Grower, Inc., Upland, CA (US)

( * ) Notice: Subject to any disclaimer, the term of this patent is extended or adjusted under 35 U.S.C. 154(b) by 0 days.

(21) Appl. No.: 10/719,264
(22) Filed: Nov. 20, 2003
(51) Int. Cl.[7] ..... A01H 5/00
(52) U.S. Cl. ..... Plt./116
(58) Field of Search ..... Plt./116

*Primary Examiner*—Anne Marie Grunberg
*Assistant Examiner*—Annette H Para

(57) ABSTRACT

A new variety of miniature rose suitable for garden decoration, having flowers of scarlet red coloration with a yellow "eyezone".

1 Drawing Sheet

Classification: The present invention relates to a new *Rosa hybrida* plant.

Variety denomination: The new plant has the varietal denomination 'WEKemilcho'.

BACKGROUND OF THE INVENTION

This invention relates to a new and distinct variety of miniature rose. It has as its seed parent the variety known as 'HARwilla' (not patented) and as its pollen parent an undisseminated seedling of my creation.

SUMMARY OF THE INVENTION

Among the features which distinguish the new variety from other presently available and commercial rose cultivars known to the inventor are the following combination of characteristics: its green styles heavily suffused with red pigmentation near the top, its single petaled flowers with a moderately large yellow zone at the base of the petal and its suffusion of red color on the rachis and the stipule. The plant has a bushy compact growing habit, suitable for outdoor garden decoration.

Asexual reproduction of the new variety by budding as performed in Kern County and Upland, Calif., shows that the foregoing and other distinguishing characteristics come true to form and are established and transmitted through succeeding asexual propagations. 'WEKemilcho' may be asexually propagated by cuttings, budding and grafting. The budding and grafting successfully occurred on the plant/rootstock *Rosa hybrida* cv. 'Dr. Huey'.

Comparison with Parents

The new rose may be distinguished from its seed parent, 'HARwilla' by the following combination of characteristics: whereas 'WEKemilcho' bears flowers of scarlet red coloration with a yellow "eyezone", 'HARwilla' bears yellow flowers blushing pink. 'WEKemilcho' bears flowers with nearly round to somewhat obovate petals, whereas 'HARwilla' bears flowers with significantly more narrow petals. The new variety is classified as a miniature rose with a bushy compact mature growing habit, whereas the seed parent is a mini-flora rose with a significantly larger and taller mature growing habit.

The new variety may be distinguished from its pollen parent, an undisseminated seedling of my creation by the following combination of characteristics: whereas 'WEKemilcho' bears small to medium size (about 3.6 to about 4.7 cm. in diameter) flowers of scarlet red coloration with a yellow "eyezone", the pollen parent bears significantly smaller flowers of blended yellow coloration. 'WEKemilcho' bears flowers of single petalage (about 5 to 6 petals), whereas the pollen parent bears flowers of significantly higher petalage. The undisseminated seedling bears light green foliage, whereas the new variety bears significantly darker foliage.

BRIEF DESCRIPTION OF ILLUSTRATION

The accompanying photograph illustrates the new variety and shows the flowering thereof from bud to full bloom depicted in color as nearly correct as it is possible to make in a color illustration of the character. Throughout this specification, color references and/or values are based upon The Colour Chart of The Royal Horticultural Society (1966) except where common terms of color definition are employed.

DESCRIPTION OF THE NEW VARIETY

The following description is of 3 to 4 year-old rose plants of the new variety grown outdoors in Upland, Calif. in the month of September. Phenotypic expression may vary with environmental, cultural and climatic conditions, as well as differences in conditions of light and soil.

FLOWER

The new variety usually bears its flowers singly, sometimes in clusters of two to three or more per stem. Flowers may be borne in irregular somewhat rounded clusters on strong short to medium length stems (about 6 to about 32 cm.). Outdoors, the plant blooms abundantly and nearly continuously during the growing season. The flowers have no fragrance.

BUD

The peduncle is about 1.8 to about 3.2 cm. in length, of average caliper (about 0.1 to about 0.15 cm. in diameter), and usually erect. It is almost entirely smooth, with very few stipitate glands. Peduncle color is between 144A and 148B often heavily suffused, especially on the side exposed to the sun, with between 183A and 187A.

Before the calyx breaks, the bud is about 0.6 to about 0.9 cm. in diameter at the widest point, about 1.2 to about 1.7 cm. in length, and pointed to somewhat ovoid in shape. The surface of the bud bears some foliaceous appendages, usually with slender entire foliaceous parts extending beyond the tip of the bud about ¼ or more of its length. Bud color is between 144A and 147B often heavily suffused, especially on the side exposed to the sun, with between 183A and 187A.

The sepals are about 1.2 to about 1.7 cm. in length and about 0.4 to about 0.6 cm. in width at the widest point. The outer surface of the sepal is between 144A and 147B often heavily suffused, especially on the side exposed to the sun, with between 183A and 187A. The inner surface of the sepal is between 138B and 137A and covered with fine wooly tomentum; sepal margins are lined with few stipitate glands and hairs.

As the petals open (after the calyx breaks), the bud is about 0.8 to about 1.1 cm. in diameter at the widest point, about 1.3 to about 1.9 cm. in length, and ovoid to moderately pointed in form. The color of the under surfaces of the newly opened petals is between 16B and 23D sometimes blushed on the area exposed to the sun with between 60A and 187B. At the point where the petal attaches, there is a moderately large zone of between 12B and 11A. The color of the upper surfaces of the newly opened petals is between 53A and 187C. At the point where the petal attaches, there is a moderately large zone of between 12A and 9A.

BLOOM

When fully open, the bloom ranges from about 3.6 to about 4.7 cm. in diameter. Petalage is single with about 5 to 6 petals and about 1 to 3 petaloids irregularly arranged. When partially open, the bloom form is very cupped to somewhat globular, and the petals are loosely cupped with petal edges slightly reflexed outward. When fully open, the bloom form is less cupped to somewhat flat, and the petals are somewhat cupped with petal edges slightly reflexed outward.

PETALS

The substance of the petals is moderately heavy to somewhat leathery and of medium to thick thickness, with upper surfaces moderately satiny to slightly velvety and under surfaces slightly shiny to matte. The petals are nearly round to somewhat obovate in shape with apices moderately mucronate to round. The petals are about 1.4 to about 2.2 cm. in length and about 1.2 to about 1.9 cm. in width at the widest point. Petal margins are entire.

NEWLY OPENED FLOWER

The under surface of the petals is between 16B and 22D sometimes blushed especially on the area exposed to the sun with between 53D and 60C. At the point where the petal attaches, there is a moderately large zone of between 12B and 11A. The upper surface of the petals is between 46A and 45A. At the point where the petal attaches, there is a moderately large zone of between 12A and 9A.

The general tonality of the newly opened flower is between 46A and 45A with a moderately large zone at the base of the petals of between 12A and 9A.

THREE-DAY-OLD FLOWER

On the under surfaces of the petals, at the point where the petal attaches, there is a moderately large zone of between 12D and 11C that is gradually suffused to between 27C and 29D toward the petal edge and is sometimes blushed on the area exposed to the sun with between 53D and 60C. The upper surface of the petals is between 53B and 46A. At the point where the petal attaches, there is a moderately large zone of between 6D and 9D sometimes lightly blushed with between 53D and 60C.

The general tonality of the three-day-old flower is between 53B and 46A with a moderately large zone at the base of the petals of between 6D and 9D.

On the spent bloom, the petals usually drop off cleanly.

In September in Upland, Calif., blooms on the bush growing outdoors generally last about four to five or more days. Cut roses from plants grown outdoors and kept at normal indoor living temperatures generally last about four to five or more days.

MALE REPRODUCTIVE ORGANS

Stamens are average in number (average about 95) and are arranged regularly about the pistils; a few are mixed with petaloids or tucked in the calyx. The filaments are of somewhat short length (about 0.2 to about 0.5 cm.), most with anthers. Filaments are between 12A and 13B in color. The anthers are of medium size for the class and all open approximately at the same time. Anther color is between 26A and 170B when immature and between 173A and 200A at maturity. Pollen is abundant.

FEMALE REPRODUCTIVE ORGANS

Pistils vary in number (average about 30). The styles are moderately even, moderately short to average in length (about 0.3 to about 0.5 cm.), somewhat thin in caliper, and moderately separated to loosely bunched. Stigma color is between 8D and 11D. Style color is between 145C and 1D often heavily suffused near the top with between 53A and 46A. Ovaries are usually all enclosed in the calyx.

Hips are of moderately short to average length (about 0.8 to about 1.3 cm.), moderately rounded to somewhat globular in form, and between 34A and 32A in color when ripe. The hip surface is very smooth with thick fleshy walls. The sepals are moderately permanent, medium in length, and usually straight in shape. The seeds are irregularly rounded, smooth in texture, approximately 2 to about 6 per hip, about 0.3 to about 0.5 cm. in diameter at the widest point and between 161B and 164C in color.

FOLIAGE

The compound leaves are usually comprised of three to five or more leaflets and are borne abundantly. The five-leaflet leaves are about 3.5 to about 7.4 cm. in length and about 2.7 to about 4.8 cm. in width at the widest point, moderately crisp to somewhat leathery in texture, and semi-glossy in finish. The terminal leaflets are about 1.7 to about 3.0 cm. in length and about 0.9 to about 1.8 cm. in width at the widest point, shaped moderately oval to somewhat ovate with moderately acuminate apices and rounded bases. Their margins are usually simply serrate.

The upper surface of the mature leaf is between 147A and 137B. The under surface of the mature leaf is between 147B and 148B. The upper surface of the young leaf is between 144A and 146C, sometimes heavily suffused with between 187B and 183C. The under surface of the young leaf is between 146B and 146C, sometimes heavily suffused with between 187B and 183C.

The rachis is moderately light in caliper and somewhat rough. The upper side is deeply grooved with numerous hairs and few stipitate glands on the edges of the grooves. The under side of the rachis is somewhat rough with few small prickles. The rachis color is between 144A and 146A sometimes suffused on the upper side with between 187B and 183C.

The stipules are about 0.5 to about 0.8 cm. in length and somewhat narrow in width (about 0.3 to about 0.5 cm.) with moderately short straight points that usually turn out at an angle of more than 45 degrees and sometimes recurve toward the stem. The stipules color is between 144A and 146A sometimes suffused on the upper side with between 187B and 183C.

The petiole is about 0.5 to about 1.1 cm. in length and about 0.1 to about 0.15 cm. in diameter at the widest point. The petiole color is between 144A and 146A sometimes suffused on the upper side with between 187B and 183C.

The plant displays an average degree of resistance to powdery mildew and rust as compared to other commercial varieties grown under comparable conditions in Upland, Calif. The plant's winter hardiness and drought/heat tolerance are yet to be determined.

GROWTH

The plant has a bushy compact low growing habit (about 46 to about 57 cm. in height and about 42 to about 52 cm. spread at the widest point), with very full branching. It displays moderately vigorous growth and the canes are of medium caliper for the class.

The color of the major stems is between 148A and 146B. They bear few medium size prickles that are about 0.3 to about 0.5 cm. in length. The medium size prickles are almost straight and angled slightly downward with a somewhat short length broad oval to somewhat rounded base; prickle color is between 177D and 176C. The major stem bears no small prickles.

The color of the branches is between 146B and 147A. They bear some medium size prickles which are of similar size and shape to the medium size prickles on the major stems; prickle color is between 160B and 162C sometimes suffused with between 187C and 183C. The branches bear no small prickles.

The color of the new shoots is between 146B and 144A sometimes heavily suffused with between 187B and 183B. They bear few medium size prickles which are of similar size and shape to the medium size prickles on the major stems; prickle color is between 187C and 183C. The shoots bear no small prickles.

I claim:

1. A new and distinct miniature rose plant of the variety substantially as described and illustrated herein.

* * * * *

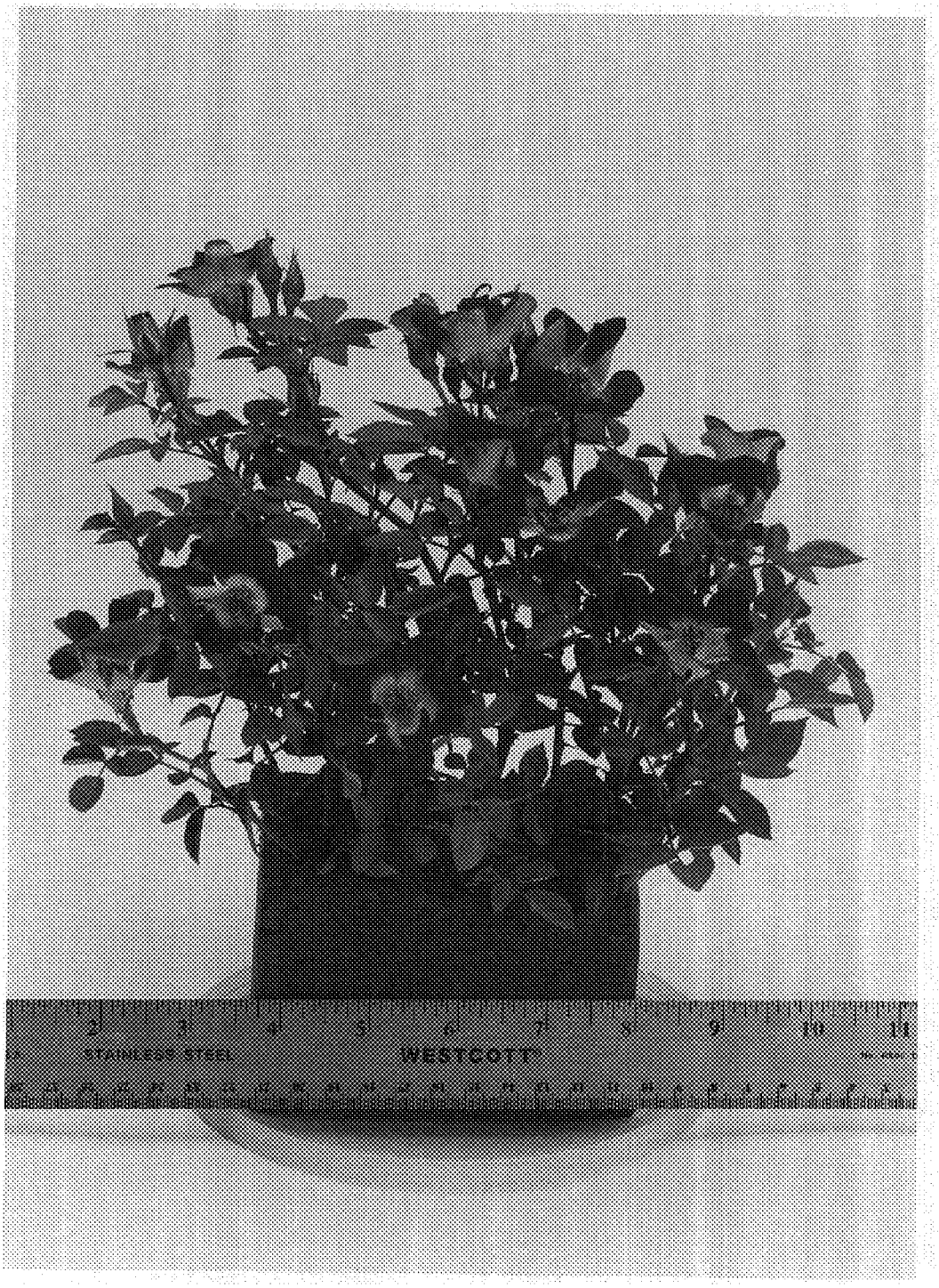
STAINLESS STEEL
WESTCOTT